United States Patent [19]

Oppenländer et al.

[11] Patent Number: 6,165,971
[45] Date of Patent: Dec. 26, 2000

[54] USE OF AMIDES OF POLYMERIZED FATTY ACIDS AS THICKENERS

[75] Inventors: Knut Oppenländer, Ludwigshafen; Michael Zirnstein, Schriesheim; Kristin Tiefensee, Westheim; Günter Oetter, Frankenthal, all of Germany

[73] Assignee: BASF Aktiengesellschaft, Ludwigshafen, Germany

[21] Appl. No.: 09/310,123

[22] Filed: May 12, 1999

[30] Foreign Application Priority Data

May 20, 1998 [DE] Germany ............... 198 22 791

[51] Int. Cl.[7] .................................................. C11D 3/32
[52] U.S. Cl. ............................................ 510/502; 510/501
[58] Field of Search ................... 510/501, 502, 510/477

[56] References Cited

U.S. PATENT DOCUMENTS

| | | | |
|---|---|---|---|
| Re. 28,913 | 7/1976 | Kelly et al. ............... | 252/547 |
| 2,537,493 | 1/1951 | Thurston et al. ............... | 260/404.5 |
| 4,429,859 | 2/1984 | Steiner et al. ............... | 252/8.8 |
| 4,636,326 | 1/1987 | Hernandez et al. . | |
| 4,795,581 | 1/1989 | Nieh et al. . | |
| 4,853,430 | 8/1989 | Stuehler et al. . | |
| 5,246,695 | 9/1993 | Hintz et al. . | |
| 5,254,271 | 10/1993 | Hamann et al. . | |
| 5,344,642 | 9/1994 | Hintz et al. . | |
| 5,472,623 | 12/1995 | Doi et al. ............... | 252/8.8 |

FOREIGN PATENT DOCUMENTS

| | | |
|---|---|---|
| 583702 A2 | 2/1994 | European Pat. Off. . |
| 19505196 | 2/1995 | Germany . |
| WO 89/11516 | 11/1989 | WIPO . |
| 95/12650 | 5/1995 | WIPO . |

*Primary Examiner*—John R. Hardee
*Attorney, Agent, or Firm*—Keil & Weinkauf

[57] ABSTRACT

The present invention relates to the use of amides of polymerized fatty acids as thickeners.

Moreover, the invention relates to aqueous compositions comprising these amides as thickeners.

15 Claims, No Drawings

USE OF AMIDES OF POLYMERIZED FATTY ACIDS AS THICKENERS

The present invention relates to the use of amides of polymerized fatty acids as thickeners and to aqueous compositions comprising these amides.

Thickeners are used widely for increasing the viscosity of aqueous preparations, for example in the field of pharmaceuticals and cosmetics. Examples of frequently used thickeners are fatty acid polyethylene glycol monoesters, fatty acid polyethylene glycol diesters, fatty acid alkanolamides, oxethylated fatty alcohols, ethoxylated glycerol fatty acid esters, cellulose ethers, sodium alginate, polyacrylic acids and neutral salts.

The use of known thickeners is, however, depending on the preparation to be thickened, associated with disadvantages. For example, the thickening effect and the salt stability of the thickener may not be satisfactory, their use may be undesired and their incorporation into the preparation to be thickened may be hindered.

Thickeners based on dimer fatty acids have proven advantageous particularly in the field of cosmetics. For example, EP-A-229 400 describes polyesters, modified with fatty acids, of polyalkylene oxide and dimerized fatty acids and their use for increasing the viscosity in surfactant-containing cosmetic, pharmaceutical and industrial preparations. As well as the desired thickening effect, these polyesters, when used in combination with sodium chloride, have a reduced corrosion effect, and, when used on the hair, an additional conditioning effect is obtained.

EP-A-507 003 describes protonated or quaternized ester amines and amidoamines of dimer fatty acids as fabric softeners in aqueous fabric softening compositions and as cleansing or care components in aqueous shower and hair shampoos and aqueous hair conditioners.

U.S. Pat. No. 4,636,326 describes thickener compositions which, in addition to a water-soluble, thermoplastic organic polymer, comprise a water-soluble polyester of dimer fatty acids and polyethylene glycols. The composition can be used for thickening aqueous hydraulic fluids and liquid concentrates for metalworking.

WO 95/12650 describes polyesters of dimer fatty acids, fatty acids and oxethylated polyalcohols as thickeners for aqueous personal care products.

U.S. Pat. No. 4,795,581 describes aqueous compositions which comprise amides of fatty acids or dimer fatty acids and higher molecular weight polyalkylene glycol diamines. The compositions can be used for thickening aqueous hydraulic fluids and aqueous cosmetic and cleansing formulations.

DE-A-195 05 196 describes low-viscosity aqueous concentrates containing at least 40% by weight of betaine surfactants and dicarboxylic acid monoamides and/or dicarboxylic acid diamides. Suitable dicarboxylic acid monoamides or diamides are reaction products of dimer fatty acid with aliphatic amines, such as, in particular, diethanolamine and dimethylaminopropylamine. The dicarboxylic acid monoamides or diamides serve to reduce the viscosity of the concentrates.

Surprisingly, we have now found that amides of polymerized fatty acids can be used as thickeners for surfactant-containing compositions, in particular for compositions comprising an alkyl or alkenyl polyglycoside.

The present invention thus relates to the use of amides of polymerized fatty acids of the formula I:

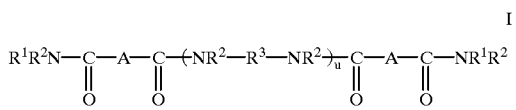

where the variables independently of one another have the following meanings:

A residue of a dimerized fatty acid having from 12 to 110 carbon atoms which remains following removal of the carboxyl groups;

$R^1$ $C_1$–$C_{12}$-alkyl or $C_3$–$C_8$-cycloalkyl, which may optionally have from 1 to 6 substituents which are chosen independently of one another from hydroxyl, $C_1$–$C_4$-alkoxy, which may optionally be substituted by 1 or 2 hydroxyl or $C_1$–$C_4$-alkoxy groups; amino, $C_1$–$C_4$-monoalkylamino and di-$C_1$–$C_4$-alkylamino, it being possible for the alkyl groups of the amino groups to be substituted independently of one another by 1 or 2 hydroxyl groups;

$R^2$ H or $C_1$–$C_4$-alkyl, which may be substituted by 1 or 2 hydroxyl groups;

$R^3$ $C_2$–$C_{12}$-alkylene which may have from 1 to 6 substituents which are chosen independently of one another from hydroxyl, $C_1$–$C_4$-alkoxy, which may be substituted by 1 or 2 hydroxyl groups; amino, $C_1$–$C_4$-monoalkylamino and di-$C_1$–$C_4$-alkylamino, it being possible for the alkyl groups of the amino groups to be substituted by 1 or 2 hydroxyl groups;

u from 0 to 20;

as thickeners.

The alkyl groups (also in groups such as alkylamino, alkoxy etc.) can be straight-chain or branched. Examples are methyl, ethyl, n-propyl, 1-methylethyl, n-butyl, 1-methylpropyl, 2-methylpropyl, 1,1-dimethylethyl, n-pentyl, n-hexyl, 2-ethylhexyl and n-dodecyl.

Preferred cycloalkyl groups are cyclopentyl and cyclohexyl.

$R^1$ is preferably a $C_1$–$C_6$-alkyl radical, which may be substituted by from 1 to 6 hydroxyl or amino groups.

$R^3$ is preferably $C_2$–$C_6$-alkylene, i.e. $(CH_2)_{2-6}$, which may optionally have one or two hydroxyl or alkoxy substituents.

u is preferably from 0 to 10, in particular from 0 to 5 and particularly preferably 0.

For the purposes of the invention, polymerized fatty acids are saturated or unsaturated fatty acids having from 12 to 110 carbon atoms, preferably from 24 to 44 carbon atoms, particularly preferably from 32 to 40 carbon atoms, which are prepared by polymerization of one or more unsaturated fatty acids.

The polymerizable fatty acids are mono- or polyunsaturated compounds having a carbon chain of from 6 to 22 carbon atoms, preferably from 12 to 22 carbon atoms, particularly preferably from 16 to 20 carbon atoms, and mixtures of these fatty acids, for example oleic acid/linoleic acid mixtures.

Polymerization of the fatty acids can lead to dimeric, trimeric, tetrameric and pentameric structures. Preference is given to dimeric and trimeric fatty acids, in particular dimeric.

The dimerized derivatives essentially comprise linear and cyclic compounds which may be unsaturated or hydrogenated, but are preferably hydrogenated.

Examples of unsaturated dimer fatty acid structures are:

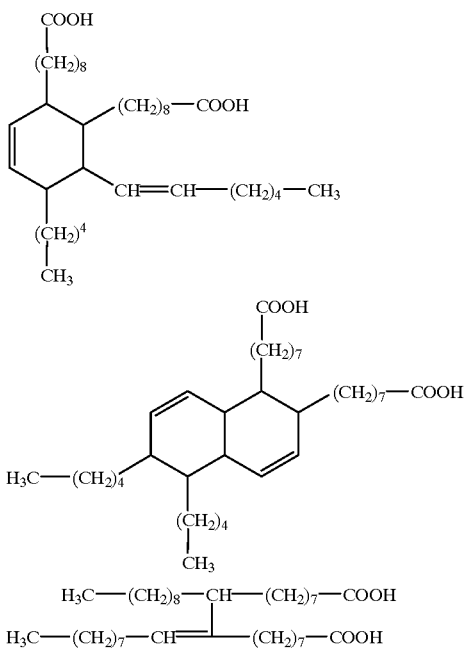

Suitable polymerized fatty acids are preferably the products obtainable commercially under the name Pripol® (Unichema) or Empol® (Henkel). These dimerized oleic/linoleic acid mixtures comprise largely linear and cyclic compounds. In addition, these products may also contain monomeric and trimeric and more highly condensed fatty acids.

Typical commercially available dimeric fatty acids have roughly the following composition:
monomeric acids: 0–15% by weight,
dimeric acids: 50–99% by weight,
tri- and higher-polymerized acids: 1–35% by weight,
the content possibly fluctuating within these limits, depending on the origin of the monomers, the polymerization process and the work-up process.

The polymerized fatty acid amides are prepared by condensation with an amine of the formula $R^1R^2NH$ and optionally with an amine of the formula $HR^2N-R^3-NHR^2$, where $R^1$ to $R^3$ are as defined above.

Suitable amines are, preferably, primary hydrophilic amines ($R^2$=H). Particular preference is given to hydroxyamines having 1, 2, 3, 4, 5 or 6 hydroxyl groups, such as monoethanolamine, 1-amino-2-propanol, 2-amino-1-propanol, 3-amino-1-propanol, aminobutanols, such as 2-amino-1-butanol, 4-amino-1-butanol, 2-amino-2-methyl-1-propanol, aminopentanols, aminohexanols and aminocyclohexanols. Suitable hydroxyamines having two or more hydroxyl groups are, for example, 1-amino-2,3-dihydroxypropane, 2-amino-1,3-dihydroxypropane and also amino sugars, such as aminosorbitol (glucamine), N-methylglucamine, glucosamine and galactosamine.

Other suitable amines are alkoxyamines, hydroxyalkoxyamines ($R^1=C_1-C_{12}$-alkyl, which is substituted by $C_1-C_4$-alkoxy or hydroxy-$C_1-C_4$-alkyl), such as 1-amino-2-methoxyethane, 1-amino-2-ethoxyethane, 2-amino-1-methoxypropane, 3-amino-1-ethoxypropane, 2-(2-aminoethoxy)ethanol and 3-(2-methoxyethoxy)-1-propanamine.

Aliphatic primary amines are also suitable, such as methylamine, ethylamine, 1-propanamine, 2-propanamine, 1-butanamine, 2-butanamine, cyclopentanamine and cyclohexanamine.

Hydrophilic secondary amines are also suitable, such as diethanolamine, N-methylethanolamine, N-ethylethanolamine, 3-(2-hydroxyethylamine)-l-propanol, diisopropanolamine and di-(2-methoxyethyl)amine.

It is also possible to use primary and secondary diamines ($R^1=C_1-C_{12}$-alkyl, which is substituted by amino, $C_1-C_4$-monoalkylamino or di-$C_1-C_4$-alkylamino; $R^2$=H, $C_1-C_4$-alkyl), for example 1,2-diaminoethane, 1,2-diaminopropane, 1,3-diaminopropane, 1,4-diaminobutane and the mono- and dimethyl derivatives thereof.

The present invention also relates to the amides of polymerized fatty acids of the formula I where $R^1$ is the residue of an amino sugar (following removal of a hydrogen atom from the amino group), and $R^2$, $R^3$, A and n are as defined above. $R^1$ is preferably the residue of an amino sugar derived from pentoses or hexoses, and is in particular an aminosorbitol, glucosamine or galactosamine radical. $R^2$ is preferably H or $CH_3$.

The polymerized fatty acid amides are prepared by methods known per se, for example by reaction of the above-mentioned amines with a polymerized fatty acid or with an ester of a polymerized fatty acid, in particular the dimethyl ester (amidation). The amidation can be carried out under usual conditions without catalyst or using an acidic or basic catalyst. Suitable acidic catalysts are, for example, acids, such as Lewis acids, for example sulfuric acid, p-toluenesulfonic acid, phosphorous acid, hypophosphorous acid, phosphoric acid, methanesulfonic acid, boric acid, aluminum chloride, boron trifluoride, tetraethyl orthotitanate, tin dioxide, tin butyldilaurate or mixtures thereof. Suitable basic catalysts are, for example, alkoxides, such as sodium methoxide or sodium ethoxide, alkali metal hydroxides, such as potassium hydroxide, sodium hydroxide or lithium hydroxide, alkaline earth metal oxides, such as magnesium oxide or calcium oxide, alkali metal and alkaline earth metal carbonates, such as sodium carbonate, potassium carbonate and calcium carbonate, phosphates, such as potassium phosphate, and complex metal hydrides, such as sodium borohydride.

The catalyst is generally used in amounts of from 0.05 to 10% by weight, preferably from 0.1 to 5% by weight, based on the total amount of the starting substances.

The reaction can be carried out in a suitable solvent or, preferably, in the absence of solvent. If a solvent is used, suitable examples are hydrocarbons, such as toluene or xylene, acetonitrile, N,N-dimethylformamide, N,N-dimethylacetamide, N-methylpyrrolidone, diethylene glycol dimethyl ether, ethylene glycol dimethyl ether, ethylene carbonate, propylene carbonate etc. In general, the solvent is distilled off during the reaction or when the reaction is complete.

When a polymerized fatty acid is used, the amidation is generally carried out at a pressure in the range from 5 mbar to atmospheric pressure and at a temperature in the range from 60 to 220° C., preferably from 120 to 180° C. When an ester of a polymerized fatty acid is used, the amidation is generally carried out at from 30 to 220° C., preferably at from 60 to 120° C., and at a pressure in the range from 5 mbar to atmospheric pressure. The reaction times are generally in the range from 2 to 20 hours. The degree of conversion can be monitored by the amount of removed reaction water or reaction alcohol or by determining the acid number and amine number of the product. Unreacted amine is generally removed when the reaction is complete in the usual manner, for example under reduced pressure and/or a stream of nitrogen.

The starting materials are generally used in equimolar amounts or in an excess of up to from about 5 to 10 mol %.

It is, however, also possible to use larger amounts of amine, in particular when readily available amines are used.

When diamines are used, a polycondensation may result (u=from 1 to 20).

Alternatively, the amides of the polymerized fatty acids can also be obtained by reacting a fatty acid chloride with the amine component by methods known per se.

The present invention also relates to aqueous compositions which comprise at least one amide of a polymerized fatty acid of the formula I as defined above and at least one surfactant.

According to one embodiment, the compositions do not comprise a betaine surfactant, in particular a betaine surfactant of the formula

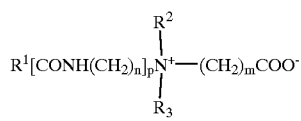

where $R^1$ is an aliphatic alkyl radical having from 8 to 22 carbon atoms, $R^2$ and $R^3$ independently of one another are an alkyl and/or hydroxyalkyl radical having from 1 to 4 carbon atoms, n and m independently of one another are numbers in the range from 1 to 5 and p is 0 or 1.

The invention further relates to aqueous compositions which comprise:
a) at least one alkyl or alkenyl polyglycoside, in particular a $C_8$–$C_{18}$-alkyl or $C_8$–$C_{16}$-alkenyl polyglycoside,
b) at least one amide of a polymerized fatty acid of the formula I as defined above,
c) optionally at least one other surfactant different from a), and
d) optionally a neutral salt.

The polyglycosides are preferably polyglucosides, which are a mixture of homologs obtained by acetylation of glucose with fatty alcohols. The mean number of glucose units per molecule is in the range from 1 to 3.

The amide of the formula I is generally present in the compositions in an amount of at least 0.1% by weight, preferably in an amount of from 0.5 to 20% by weight, based on the total weight of the product.

The surfactant present in the products according to the invention may be anionic, nonionic, cationic or amphoteric. It has been found that the amides of the formula I are also compatible with anionic surfactants.

Examples of surfactants are alkyl polyglycosides, fatty alcohol sulfates, fatty alcohol sulfonates, fatty alcohol ether sulfates, fatty alcohol ether sulfonates, alkanesulfonates, fatty alcohol ethoxylates, fatty alcohol phosphates, alkylbetaines, sorbitan esters, POE-sorbitan esters, sugar fatty acid esters, fatty acid polyglycerol esters, fatty acid partial glycerides, fatty acid carboxylates, fatty alcohol sulfosuccinates, fatty acid sarcosinates, fatty acid isethionates, fatty acid taurates, 40 citric esters, silicone copolymers, fatty acid polyglycol esters, fatty acid amides, fatty acid alkanolamides, quaternary ammonium compounds, alkylphenol oxethylates and fatty amine oxethylates.

The compositions according to the invention preferably comprise an anionic surfactant and/or a nonionic surfactant, the anionic surfactant particularly preferably being a fatty alcohol sulfate, fatty alcohol sulfonate, fatty alcohol ether sulfonate, alkanesulfonate and, in particular, a fatty alcohol ether sulfate, and the nonionic surfactant being an alkyl or alkenyl polyglycoside.

A further preferred embodiment is an aqueous composition in the form of a pourable solution which comprises at least one amide of the formula I and at least one $C_8$–$C_{16}$-alkyl or $C_8$–$C_{16}$-alkenyl polyglycoside. This composition generally comprises from 10 to 95% by weight, preferably from 60 to 90% by weight, of the amide, based on the total amount of the two components. The total amount of the components in the composition is generally from 30 to 95% by weight.

For additional thickening, the compositions according to the invention may comprise a neutral salt, in particular sodium sulfate and, preferably, sodium chloride. The neutral salt is generally present in an amount of from 0.1 to 10% by weight, in particular from 0.5 to 10% by weight.

Furthermore, the compositions according to the invention can comprise customary auxiliaries and additives known to the person skilled in the art, for example cosolvents such as ethylene glycol, propylene glycol, glycerol, lanolin derivatives, cholesterol derivatives, isopropyl myristate, isopropyl palmitate, electrolytes, dyes, preservatives, and acids (for example lactic acid or citric acid) etc.

In each case based on the total weight of the ingredients (except water), the products according to the invention generally comprise:
from 0.5 to 50% by weight, preferably from 1 to 25% by weight, of at least one amide of the formula I,
from 50 to 99.5% by weight, preferably from 65 to 90% by weight, of at least one surfactant and
from 0 to 50% by weight, preferably from 0.5 to 30% by weight, of at least one neutral salt,
the amounts totaling 100% by weight.

According to a preferred embodiment, the compositions according to the invention comprise (based on the total weight of the ingredients):
a) from 10 to 90% by weight, preferably from 15 to 85% by weight, of at least one $C_8$–$C_{16}$-alkyl or $C_8$–$C_{16}$-alkenyl polyglycoside;
b) from 0.5 to 50% by weight, preferably from 1 to 25% by weight, of at least one amide of the formula I;
c) from 10 to 90% by weight, preferably from 15 to 85% by weight, of at least one anionic surfactant, in particular an alkyl ether sulfate, and
d) from 0 to 50% by weight, preferably from 0.5 to 30% by weight, of at least one neutral salt,
the amounts totaling 100% by weight.

These compositions according to the invention are prepared in the usual manner, it being possible to use the amides of the polymerized fatty acids as such or as an aqueous solution. The thickener is generally stirred into the aqueous composition.

The compositions according to the invention are, in particular, cosmetic (shampoos), pharmaceutical or dietetic compositions. The amides of the polymerized fatty acids can, however, also be used in industrial preparations, such as hydraulic fluids, cleaning preparations, crop-treatment products, printing inks, coating materials and preparations for animal nutrition.

The examples below illustrate the invention without limiting it.

The abbreviations used in the examples have the following meanings:
AV: acid value
OHV: hydroxyl value

EXAMPLES

Example 1

30.8 g of 1-amino-2-propanol and 0.1 g of potassium carbonate were added, at 80° C., to 115.0 g of Pripol 1025

(polymerized fatty acid, Unichema; AV=194 mg of KOH/g), and the mixture was stirred for 12 hours at from 155 to 160° C. under $N_2$ as protective gas. The reaction water which formed was distilled off. This gave 132 g of the corresponding amide.

AV=1.5 mg of KOH/g

OHV=149 mg of KOH/g

Example 2

18.3 g of monoethanolamine and 0.1 g of potassium carbonate were added, at 80° C., to 85.2 g of Pripol 1009 (polymerized fatty acid, Unichema; AV=193 mg of KOH/g), and the mixture was stirred for 6 hours at from 150 to 155° C. under $N_2$ as protective gas. The reaction water which formed was distilled off. This gave 96 g of the corresponding amide.

AV=6.6 mg of KOH/g

OHV=160 mg of KOH/g

Example 3

85.8 g of Pripol 1098 (polymerized fatty acid, Unichema; AV=198 mg of KOH/g) and 0.14 g of potassium carbonate were added, at 150° C., to 54.7 g of aminosorbitol, and the mixture was stirred for 6 hours at 150° C. under $N_2$ as protective gas. The reaction water which formed was distilled off. This gave 124 g of the corresponding amide.

AV=8.2 mg of KOH/g

OHV=583 mg of KOH/g

Example 4

87.2 g of Pripol 1009 (polymerized fatty acid, Unichema; AV=193 mg of KOH/g) and 2.84 g of 50% strength hypophosphorous acid were added, at 150° C., to 54.7 g of aminosorbitol, and the mixture was stirred for 10 hours at 150° C. under $N_2$ as protective gas. The reaction water which formed was distilled off. This gave 120 g of the corresponding amide.

AV=14.0 mg of KOH/g

OHV=506 mg of KOH/g

Example 5

58.1 g of Pripol 1009 (polymerized fatty acid, Unichema; AV=193 mg of KOH/g) and 0.10 g of potassium carbonate were added, at 150° C., to 39.0 g of N-methylglucamine, and the mixture was stirred for 7 hours at 150° C. under $N_2$ as protective gas. The reaction water which formed was distilled off. This gave 79 g of the corresponding amide.

AV=5.8 mg of KOH/g

OHV=448 mg of KOH/g

Example 6

The following composition was prepared: Plantaren 2000 ($C_8$–$C_{16}$-alkyl polyglycoside; 50% strength) 160 g Texapon NSO (sodium lauryl ether sulfate; 28% strength) 220 g demineralized water 610 g The pH of the composition was adjusted to 6.0 by adding citric acid. 3% by weight of sodium chloride, based on the total weight of the composition, was then added. The resulting composition then had a viscosity of 12.5 mPas. In each case 2% by weight, 2.5% by weight and 3% by weight of the amide obtained as in Example 1 or as in Example 2 were then stirred into equal parts of this composition, and the viscosity was determined. The viscosity was measured using a HAAKE VT 500 apparatus, measuring device PK5-1°; temperature 20° C.; shear rate 30 $s^{-1}$. The resulting viscosities (in mPas) are listed in the table below.

| Amide | 0% | 2.5% | 3% |
|---|---|---|---|
| Example 1 | 12.5 | 1500 | 1800 |
| Example 2 | 12.5 | 2150 | — |
| Example 3 | 12.5 | — | 4400 |
| Example 4 | 12.5 | — | 3750 |
| Example 5 | 12.5 | — | 2750 |

259/cb/iT

We claim:

1. An aqueous composition comprising at least one surfactant, and at least one amide of a polymerized fatty acid of the formula I,

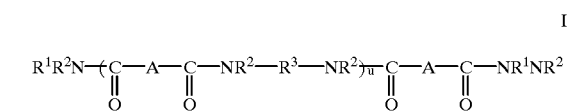

where the variables independently of one another have the following meanings:

A residue of a dimerized fatty acid having from 12 to 110 carbon atoms;

$R^1$ $C_1$–$C_{12}$-alkyl or $C_3$–$C_8$-cycloalkyl, which may optionally have from 1 to 6 substituents which are chosen independently of one another from hydroxyl, $C_1$–$C_4$-alkoxy, which may optionally be substituted by 1 or 2 hydroxyl or $C_1$–$C_4$-alkoxy groups;

$R^2$ H or $C_1$–$C_4$-alkyl, which may be substituted by 1 or 2 hydroxyl groups; $R^3$ $C_2$–$C_{12}$-alkylene which may have from 1 to 6 substituents which are chosen independently from one another from hydroxyl, $C_1$–$C_4$-alkoxy, which may be substituted by 1 or 2 hydroxyl groups; amino, $C_1$–$C_4$-monoalkylamino and di-$C_1$–$C_4$-alkylamino, it being possible for the alkyl groups of the amino groups to be substituted by 1 or 2 hydroxyl groups;

u from 0 to 20.

2. A composition as claimed in claim 1, where A is the residue of a dimerized fatty acid having from 22 to 42 carbon atoms.

3. A composition as claimed in claim 1, where $R^1$ is a $C_1$–$C_6$-alkyl radical substituted by from 1 to 6 hydroxyl groups.

4. A composition as claimed in claim 1 in the form of a cosmetic composition.

5. A composition as claimed in claim 1 comprising from 0.5 to 20% by weight of the amide of the formula I.

6. A composition as claimed in claim 1, where A is the residue of a dimerized fatty acid having from 30 to 38 carbon atoms.

7. An aqueous composition comprising:

a) at least one alkyl or alkenyl polyglycoside, b) at least one amide of a polymerized fatty acid of the formula I

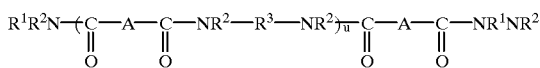

where the variables independently of one another have the following meanings:

A residue of a dimerized fatty acid having from 12 to 110 carbon atoms;

$R^1$ $C_1$–$C_{12}$-alkyl or $C_3$–$C_8$-cycloalkyl, which may optionally have from 1 to 6 substituents which are chosen independently of one another from hydroxyl, $C_1$–$C_4$-alkoxy, which may optionally be substituted by 1 or 2 hydroxyl or $C_1$–$C_4$-alkoxy groups;

$R^2$ H or $C_1$–$C_4$-alkyl, which may be substituted by 1 or 2 hydroxyl groups;

$R^3$ $C_2$–$C_{12}$-alkylene which may have from 1 to 6 substituents which are chosen independently from one another from hydroxyl, $C_1$–$C_4$-alkoxy, which may be substituted by 1 or 2 hydroxyl groups; amino, $C_1$–$C_4$-monoalkylamino and di-$C_1$–$C_4$-alkylamino, it being possible for the alkyl groups of the amino groups to be substituted by 1 or 2 hydroxyl groups;

u from 0 to 20.

8. A composition as claimed in claim 7, where A is the residue of a dimerized fatty acid having from 22 to 42 carbon atoms.

9. A composition as claimed in claim 7, wherein $R^1$ is a $C_1$–$C_6$-alkyl radical substituted by from 1 to 6 hydroxyl groups.

10. A composition as claimed in claim 7 comprising from 0.5 to 20% by weight of the amide of the formula I.

11. A composition as claimed in claim 7, comprising:
a) from 10 to 90% by weight of an alkyl or alkenyl polyglycoside,
b) from 0.5 to 50% by weight of an amide of the formula I,
c) from 10 to 90% by weight of an anionic surfactant, and
d) from 0 to 50% by weight of a neutral salt, based on the total weight of the components.

12. A composition as claimed in claim 7 in the form of a cosmetic composition.

13. A composition as claimed in claim 7, comprising
a) from 10 to 95% by weight of an amide of the formula I and
b) from 5 to 90% by weight of an alkyl or alkenyl polyglycoside, based on the total weight of the two components.

14. A composition as claimed in claim 7, where A is the residue of a dimerized fatty acid having from 30 to 38 carbon atoms.

15. A method of increasing the viscosity of surfactant-containing compositions which comprises adding to the composition a thickening amount of at least one amide of polymerized fatty acids of the formula I

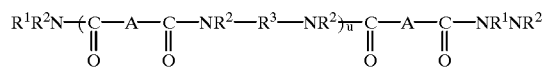

where the variables independently of one another have the following meanings:

A residue of a dimerized fatty acid having from 12 to 110 carbon atoms;

$R^1$ $C_1$–$C_{12}$-alkyl or $C_3$–$C_8$-cycloalkyl, which may optionally have from 1 to 6 substituents which are chosen independently of one another from hydroxyl, $C_1$–$C_4$-alkoxy, which may optionally be substituted by 1 or 2 hydroxyl or $C_1$–$C_4$-alkoxy groups;

$R^2$ H or $C_1$–$C_4$-alkyl, which may be substituted by 1 or 2 hydroxyl groups;

$R^3$ $C_2$–$C_{12}$-alkylene which may have from 1 to 6 substituents which are chosen independently from one another from hydroxyl, $C_1$–$C_4$-alkoxy, which may be substituted by 1 or 2 hydroxyl groups; amino, $C_1$–$C_4$-monoalkylamino and di-$C_1$–$C_4$-alkylamino, it being possible for the alkyl groups of the amino groups to be substituted by 1 or 2 hydroxyl groups;

u from 0 to 20.

* * * * *